(12) United States Patent
de Baetselier et al.

(10) Patent No.: US 7,060,790 B1
(45) Date of Patent: Jun. 13, 2006

(54) **PEPTIDES AND NUCLEIC ACIDS DERIVED FROM *EISENIA FOETIDA* AND THE USE THEREOF**

(75) Inventors: Patrick de Baetselier, Berchem (BE); Alain Beschin, Bouffioulx (BE)

(73) Assignee: Vlaams Interuniversitair Instituut voor Biotechnologie VZW, Zwijnaarde (BE)

( * ) Notice: Subject to any disclaimer, the term of this patent is extended or adjusted under 35 U.S.C. 154(b) by 0 days.

(21) Appl. No.: 09/596,101

(22) Filed: Jun. 16, 2000

Related U.S. Application Data

(63) Continuation of application No. PCT/EP98/08169, filed on Dec. 16, 1998.

(30) Foreign Application Priority Data

Dec. 17, 1997 (EP) .................................. 97203974

(51) Int. Cl.
A61K 38/00 (2006.01)
A61K 35/12 (2006.01)
A61K 35/24 (2006.01)
A01N 63/00 (2006.01)
C12P 21/00 (2006.01)

(52) U.S. Cl. ..................... 530/324; 530/300; 424/93.1; 424/520; 424/537; 435/69.1

(58) Field of Classification Search ............... 435/69.1, 435/389.2, 388.22, 388.26, 388.6, 389.1
See application file for complete search history.

(56) References Cited

FOREIGN PATENT DOCUMENTS

| EP | 0 383 533 A | 8/1990 |
|---|---|---|
| WO | WO 99/31229 | 6/1999 |

OTHER PUBLICATIONS

Beschin et al, The Journal of Biological Chemistry, vol. 278, No. 38, Sep. 18, 1998, p. 24948-24954.*
Bilej et al, Immunology Letters, 45, 1995, p. 123-128.*
Bilej et al, European Cytokine Network, Mar.-Apr. 1994, vol.5, No. 2, p. 99.*
Lassegues et al, Euro. J. Biochem., 246:756-762.*
Lucas et al, Science, vol. 263, Feb. 11, 1994, p. 814-817.*
Bilej et al, European Cytokine Network, Mar.-Apr. 1994.*
Bilej et al, Immunology Letters, 45, 1995.*
Bilej et al (European Cytokine Network, Mar.-Apr. 1994).*
Bilej at al (Immunology Letters, 45, 1995).*
Thomas E. Creighton, in his book, "Proteins: Structures and Molecular Properties, 1984", (pp. 314-315).*
Thomas E. Creighton, in his book "Protein Structure: A Practical Approach, 1989; pp. 184-186".*
Nosoh, Y. et al in "Protein Stability and Stabilization through Protein Engineering, 1991" (chapter 7, p. 197, second paragraph).*
Bystryn (Cancer and Metastasis Reviews, 9:81-18).*
Kyd et al, (Vaccine 18 (2000), 398-406)).*
Samukawa et al, ( The Journal of Infectious Diseases, 2000, 181:1842-5).*
Gu et al, Infection and Immunity, May 1998, p. 1891-1897.*
Odeh (Cytokine, Apr. 7,14(1):11-8).*
Fox (Biotechnology, vol. 12, Feb. 1994).*
Beschin et al., "Identification and Cloning of a Glucan- and Lipopolysaccharide-binding Protein from *Eisenia foetida* Earthworm Involved in the Activation of Prophenoloxidase Cascade", *The Journal of Biological Chemistry*, vol. 273, No. 38, pp. 24948-24954, Sep. 18, 1998.
Bilej et al., "Identification of a cytolytic protein in the coelomic fluid of *Eisenia foetida* earthworms", *Immunology Letters*, vol. 45, No. 1-2, pp. 123-128, Feb. 1995.
Bilej et al., "Identification of TNF-Like Activity in Earthworms", *European Cytokine Network*, vol. 5, No. 2, p. 99, 1994.
Lassegues et al., "Sequence and expression of an *Eisenia-fetida*-derived cDNA clone that encodes the 40-kDa fetidin antibacterial protein", *Eur. J. Biochem.*, vol. 246, No. 3, pp. 756-762, Jun. 15, 1997.
Lucas et al., "Mapping the Lectin-Like Activity of Tumor Necrosis Factor", *Science*, vol. 263, pp. 814-817, Feb. 11, 1994.
PCT International Search Report, PCT/EP98/08169, dated Jul. 6, 1999, 7 pages, listing the above-identified documents.
PCT International Perliminary Examination Report, PCT/EP98/08169, dated Mar. 17, 2000, 8 pages.

* cited by examiner

*Primary Examiner*—Nita Minnifield
*Assistant Examiner*—Vanessa L. Ford
(74) *Attorney, Agent, or Firm*—TraskBritt

(57) ABSTRACT

The invention concerns *Eisenia foetida* polypeptides and peptides, particularly recombinant polypeptides, which are useful in tumour therapy, microbial infection, inflammation or immunology. The invention also relates to a process for preparing the above-mentioned polypeptides and peptides. Furthermore the invention concerns nucleic acids coding for said polypeptides and peptides.

2 Claims, 6 Drawing Sheets

SEQUENCE LISTING

<160> NUMBER OF SEQ ID NOS: 15

<210> SEQ ID NO 1
<211> LENGTH: 13
<212> TYPE: PRT
<213> ORGANISM: Eisenia foetida

<400> SEQUENCE: 1

```
Ser Gly Glu Ile Asp Ile Ile Glu Thr Ile Gly Asn Arg
1               5                   10
```

<210> SEQ ID NO 2
<211> LENGTH: 1155
<212> TYPE: DNA
<213> ORGANISM: Eisenia foetida
<220> FEATURE:
<221> NAME/KEY: CDS
<222> LOCATION: (1)..(1152)
<223> OTHER INFORMATION:
<221> NAME/KEY: sig_peptide
<222> LOCATION: (1)..(51)
<223> OTHER INFORMATION:
<221> NAME/KEY: mat_peptide
<222> LOCATION: (52)..()
<223> OTHER INFORMATION:

<400> SEQUENCE: 2

```
atg agg tgg act ttg gtg gtc ttg tgt ctg ctg ttc ggt gaa ggg ttc      48
Met Arg Trp Thr Leu Val Val Leu Cys Leu Leu Phe Gly Glu Gly Phe
        -15                 -10                 -5 gcc ttc acc gac tgg gat caa tat cac atc gtc tgg cag gac gaa ttc      96
Ala Phe Thr Asp Trp Asp Gln Tyr His Ile Val Trp Gln Asp Glu Phe
-1   1               5                   10                  15 gat tac ttt gat ggc gcg aag tgg caa cat gag gtc aca gca act ggc     144
Asp Tyr Phe Asp Gly Ala Lys Trp Gln His Glu Val Thr Ala Thr Gly
                20                  25                  30 gga ggg aac agc gaa ttc caa ctg tac aca cag gat ggg gcc aac agc     192
Gly Gly Asn Ser Glu Phe Gln Leu Tyr Thr Gln Asp Gly Ala Asn Ser
            35                  40                  45 ttc gtt cga gat gga aag ctt ttc att aag ccg acg ttg ctg gct gac     240
Phe Val Arg Asp Gly Lys Leu Phe Ile Lys Pro Thr Leu Leu Ala Asp
        50                  55                  60 aac atc aac cca cag acg ggt gcg cca ttt gga acc gat ttc atg tac     288
Asn Ile Asn Pro Gln Thr Gly Ala Pro Phe Gly Thr Asp Phe Met Tyr
65                  70                  75 aat gga gtt cta gat gtc tgg gct atg tac ggg gcc tgc acg aat acg     336
Asn Gly Val Leu Asp Val Trp Ala Met Tyr Gly Ala Cys Thr Asn Thr
80                  85                  90                  95 gac aac aac gga tgc tac agg acg gga gcc gct ggc gac att cca ccg     384
Asp Asn Asn Gly Cys Tyr Arg Thr Gly Ala Ala Gly Asp Ile Pro Pro
                100                 105                 110 gcc atg tcg gca cga gtt cga acc ttc cag aaa tac agc ttc acc cac     432
Ala Met Ser Ala Arg Val Arg Thr Phe Gln Lys Tyr Ser Phe Thr His
            115                 120                 125 gga cgc gtt gtc gtt cac gcc aag atg ccc gtc gga gac tgg ctc tgg     480
Gly Arg Val Val Val His Ala Lys Met Pro Val Gly Asp Trp Leu Trp
        130                 135                 140 cca gcc att tgg atg ttg ccg gag gat tgg gtc tat ggc gga tgg cct     528
Pro Ala Ile Trp Met Leu Pro Glu Asp Trp Val Tyr Gly Gly Trp Pro
            145                 150                 155 cga tcg ggc gag atc gac atc att gaa aca atc ggc aac cga gat ttc     576
Arg Ser Gly Glu Ile Asp Ile Ile Glu Thr Ile Gly Asn Arg Asp Phe
160                 165                 170                 175 aag aac act ggt gga gag ttc ctt gga att cag aag atg gga tca acg     624
Lys Asn Thr Gly Gly Glu Phe Leu Gly Ile Gln Lys Met Gly Ser Thr
                180                 185                 190 atg cac tgg ggt cca gga tgg gac gac aac cga tac tgg ctg acc agc     672
Met His Trp Gly Pro Gly Trp Asp Asp Asn Arg Tyr Trp Leu Thr Ser
            195                 200                 205
```

|  |  |  |  |  |  |  |  |  |  |  |  |  |  |  |  |
|---|---|---|---|---|---|---|---|---|---|---|---|---|---|---|---|
| ctt | ccg | aaa | cac | tca | gac | gat | tgg | aac | tac | ggt | gac | aac | ttc | cac | acg | 720
| Leu | Pro | Lys | His | Ser | Asp | Asp | Trp | Asn | Tyr | Gly | Asp | Asn | Phe | His | Thr |
|  | 210 |  |  |  | 215 |  |  |  | 220 |

```
ctt ccg aaa cac tca gac gat tgg aac tac ggt gac aac ttc cac acg        720
Leu Pro Lys His Ser Asp Asp Trp Asn Tyr Gly Asp Asn Phe His Thr
    210             215                 220 ttc tgg ttc gac tgg agt ccc aac gga ctg agg ttc ttc gta gac gac        768
Phe Trp Phe Asp Trp Ser Pro Asn Gly Leu Arg Phe Phe Val Asp Asp
225                 230                 235 gag aac cag gct ctg ctc gat gtt cct tat cct ctg att gat gcg aat        816
Glu Asn Gln Ala Leu Leu Asp Val Pro Tyr Pro Leu Ile Asp Ala Asn
240                 245                 250                 255 cca tgg tgg gtg gat ttc tgg gag tgg gga aag ccc tgg ctt cct caa        864
Pro Trp Trp Val Asp Phe Trp Glu Trp Gly Lys Pro Trp Leu Pro Gln
                260                 265                 270 tac gaa aat gac aat cca tgg gct gga gga acg aac ctg gct ccc ttc        912
Tyr Glu Asn Asp Asn Pro Trp Ala Gly Gly Thr Asn Leu Ala Pro Phe
            275                 280                 285 gac caa aat ttc cac ttc att ctg aac gtg gct gtc gga gga acg aac        960
Asp Gln Asn Phe His Phe Ile Leu Asn Val Ala Val Gly Gly Thr Asn
        290                 295                 300 ggc ttc atc ccg gac ggt tgc atc aat cgc ggc gga gac ccg gcc ctg       1008
Gly Phe Ile Pro Asp Gly Cys Ile Asn Arg Gly Gly Asp Pro Ala Leu
305                 310                 315 cag aag ccg tgg agc aat ggg gac tgg tac aac gat gca atg agg aaa       1056
Gln Lys Pro Trp Ser Asn Gly Asp Trp Tyr Asn Asp Ala Met Arg Lys
320                 325                 330                 335 ttc ttc gac gcc aga gga aac tgg aag tgg acg tgg gat gac gag gga       1104
Phe Phe Asp Ala Arg Gly Asn Trp Lys Trp Thr Trp Asp Asp Glu Gly
                340                 345                 350 gac aac aat gcc atg cag gtc gat tac atc cga gtc tac aag cgc aac       1152
Asp Asn Asn Ala Met Gln Val Asp Tyr Ile Arg Val Tyr Lys Arg Asn
            355                 360                 365 tga                                                                    1155

<210> SEQ ID NO 3
<211> LENGTH: 384
<212> TYPE: PRT
<213> ORGANISM: Eisenia foetida

<400> SEQUENCE: 3

Met Arg Trp Thr Leu Val Val Leu Cys Leu Leu Phe Gly Glu Gly Phe
        -15                 -10                 -5

Ala Phe Thr Asp Trp Asp Gln Tyr His Ile Val Trp Gln Asp Glu Phe
-1   1              5                   10                  15

Asp Tyr Phe Asp Gly Ala Lys Trp Gln His Glu Val Thr Ala Thr Gly
                20                  25                  30

Gly Gly Asn Ser Glu Phe Gln Leu Tyr Thr Gln Asp Gly Ala Asn Ser
            35                  40                  45

Phe Val Arg Asp Gly Lys Leu Phe Ile Lys Pro Thr Leu Leu Ala Asp
        50                  55                  60

Asn Ile Asn Pro Gln Thr Gly Ala Pro Phe Gly Thr Asp Phe Met Tyr
    65                  70                  75

Asn Gly Val Leu Asp Val Trp Ala Met Tyr Gly Ala Cys Thr Asn Thr
80                  85                  90                  95

Asp Asn Asn Gly Cys Tyr Arg Thr Gly Ala Ala Gly Asp Ile Pro Pro
                100                 105                 110

Ala Met Ser Ala Arg Val Arg Thr Phe Gln Lys Tyr Ser Phe Thr His
            115                 120                 125

Gly Arg Val Val Val His Ala Lys Met Pro Val Gly Asp Trp Leu Trp
        130                 135                 140
```

```
Pro Ala Ile Trp Met Leu Pro Glu Asp Trp Val Tyr Gly Gly Trp Pro
    145                 150                 155
Arg Ser Gly Glu Ile Asp Ile Ile Glu Thr Ile Gly Asn Arg Asp Phe
160                 165                 170                 175
Lys Asn Thr Gly Gly Glu Phe Leu Gly Ile Gln Lys Met Gly Ser Thr
                180                 185                 190
Met His Trp Gly Pro Gly Trp Asp Asp Asn Arg Tyr Trp Leu Thr Ser
            195                 200                 205
Leu Pro Lys His Ser Asp Asp Trp Asn Tyr Gly Asp Asn Phe His Thr
        210                 215                 220
Phe Trp Phe Asp Trp Ser Pro Asn Gly Leu Arg Phe Phe Val Asp Asp
    225                 230                 235
Glu Asn Gln Ala Leu Leu Asp Val Pro Tyr Pro Leu Ile Asp Ala Asn
240                 245                 250                 255
Pro Trp Trp Val Asp Phe Trp Glu Trp Gly Lys Pro Trp Leu Pro Gln
                260                 265                 270
Tyr Glu Asn Asp Asn Pro Trp Ala Gly Gly Thr Asn Leu Ala Pro Phe
            275                 280                 285
Asp Gln Asn Phe His Phe Ile Leu Asn Val Ala Val Gly Gly Thr Asn
        290                 295                 300
Gly Phe Ile Pro Asp Gly Cys Ile Asn Arg Gly Gly Asp Pro Ala Leu
    305                 310                 315
Gln Lys Pro Trp Ser Asn Gly Asp Trp Tyr Asn Asp Ala Met Arg Lys
320                 325                 330                 335
Phe Phe Asp Ala Arg Gly Asn Trp Lys Trp Thr Trp Asp Asp Glu Gly
                340                 345                 350
Asp Asn Asn Ala Met Gln Val Asp Tyr Ile Arg Val Tyr Lys Arg Asn
            355                 360                 365

<210> SEQ ID NO 4
<211> LENGTH: 33
<212> TYPE: DNA
<213> ORGANISM: Artificial Sequence
<220> FEATURE:
<223> OTHER INFORMATION: PCR Primer
<221> NAME/KEY: misc_feature
<222> LOCATION: (2)..(2)
<223> OTHER INFORMATION: Inosine
<221> NAME/KEY: misc_feature
<222> LOCATION: (5)..(5)
<223> OTHER INFORMATION: Inosine
<221> NAME/KEY: misc_feature
<222> LOCATION: (8)..(8)
<223> OTHER INFORMATION: Inosine
<221> NAME/KEY: misc_feature
<222> LOCATION: (14)..(14)
<223> OTHER INFORMATION: Inosine
<221> NAME/KEY: misc_feature
<222> LOCATION: (25)..(25)
<223> OTHER INFORMATION: Inosine
<221> NAME/KEY: misc_feature
<222> LOCATION: (28)..(28)
<223> OTHER INFORMATION: Inosine

<400> SEQUENCE: 4
tnacngantg ggancaagta tcatngtntg gca                           33

<210> SEQ ID NO 5
<211> LENGTH: 32
<212> TYPE: DNA
<213> ORGANISM: Artificial sequence
```

```
<220> FEATURE:
<223> OTHER INFORMATION: PCR Primer
<221> NAME/KEY: misc_feature
<222> LOCATION: (3)..(3)
<223> OTHER INFORMATION: Inosine
<221> NAME/KEY: misc_feature
<222> LOCATION: (6)..(6)
<223> OTHER INFORMATION: Inosine
<221> NAME/KEY: misc_feature
<222> LOCATION: (9)..(9)
<223> OTHER INFORMATION: Inosine
<221> NAME/KEY: misc_feature
<222> LOCATION: (12)..(12)
<223> OTHER INFORMATION: Inosine
<221> NAME/KEY: misc_feature
<222> LOCATION: (19)..(19)
<223> OTHER INFORMATION: Inosine

<400> SEQUENCE: 5
aangtntgna anttgatcnc cgatagattc ca                           32

<210> SEQ ID NO 6
<211> LENGTH: 37
<212> TYPE: DNA
<213> ORGANISM: Artificial sequence
<220> FEATURE:
<223> OTHER INFORMATION: PCR Primer

<400> SEQUENCE: 6
ggggatccat gcattcaccg actgggatca atatcac                      37

<210> SEQ ID NO 7
<211> LENGTH: 29
<212> TYPE: DNA
<213> ORGANISM: Artificial sequence
<220> FEATURE:
<223> OTHER INFORMATION: PCR Primer

<400> SEQUENCE: 7
ccgtcgactc agttgcgctt gtagactcg                               29

<210> SEQ ID NO 8
<211> LENGTH: 30
<212> TYPE: PRT
<213> ORGANISM: Eisenia foetida

<400> SEQUENCE: 8

Phe Thr Asp Trp Asp Gln Tyr His Ile Val Trp Gln Asp Glu Phe Asp
1               5                  10                  15

Tyr Phe Asp Gly Ala Lys Trp Gln His Glu Val Thr Ala Thr
            20                  25                  30

<210> SEQ ID NO 9
<211> LENGTH: 3
<212> TYPE: PRT
<213> ORGANISM: Eisenia foetida

<400> SEQUENCE: 9

Val Tyr Lys
1

<210> SEQ ID NO 10
<211> LENGTH: 11
<212> TYPE: PRT
<213> ORGANISM: Eisenia foetida
```

```
<400> SEQUENCE: 10

Asn Thr Gly Gly Glu Phe Leu Gly Ile Gln Lys
1               5                   10

<210> SEQ ID NO 11
<211> LENGTH: 16
<212> TYPE: PRT
<213> ORGANISM: Eisenia foetida

<400> SEQUENCE: 11

Met Gly Ser Thr Met His Trp Gly Pro Gly Trp Asp Asp Asn Glu Arg
1               5                   10                  15

<210> SEQ ID NO 12
<211> LENGTH: 8
<212> TYPE: PRT
<213> ORGANISM: Eisenia foetida

<400> SEQUENCE: 12

Tyr Trp Leu Thr Ser Leu Pro Lys
1               5

<210> SEQ ID NO 13
<211> LENGTH: 13
<212> TYPE: PRT
<213> ORGANISM: Eisenia foetida

<400> SEQUENCE: 13

Ser Gly Glu Ile Asp Ile Ile Glu Thr Ile Gly Asn Arg
1               5                   10

<210> SEQ ID NO 14
<211> LENGTH: 7
<212> TYPE: PRT
<213> ORGANISM: Unknown
<220> FEATURE:
<223> OTHER INFORMATION: Sequence of TIP region of Tumour Necrosis
      Factor (TNF) that exhibits lectin-like activity

<400> SEQUENCE: 14

Thr Pro Glu Gly Ala Glu Ala
1               5

<210> SEQ ID NO 15
<211> LENGTH: 6
<212> TYPE: PRT
<213> ORGANISM: Unknown
<220> FEATURE:
<223> OTHER INFORMATION: Sequence of TIP region of Tumour Necrosis
      Factor (TNF) that exhibits lectin-like activity

<400> SEQUENCE: 15

Thr Pro Glu Gly Ala Glu
1               5
```

PEPTIDES AND NUCLEIC ACIDS DERIVED FROM *EISENIA FOETIDA* AND THE USE THEREOF

CROSS-REFERENCE TO RELATED APPLICATION

This application claims continuation status under 35 U.S.C. §§ 120 & 365(c) from co-pending patent application PCT/EP98/08169 filed on Dec. 16, 1998 designating the United States of America, which itself claims priority from European Patent Application EP 97203974.7 filed on Dec. 17, 1997.

BACKGROUND OF THE INVENTION

1. Field of the Invention

The invention relates to *Eisenia foetida* polypeptides and peptides, particularly to recombinant polypeptides useful in tumour therapy, microbial infection, inflammation or immunology.

The invention also relates to a process for preparing the above-said polypeptides and peptides.

Furthermore, the invention concerns nucleic acids coding for said polypeptides and peptides.

2. State of the Art

Tumour Necrosis Factor a (TNF-α) is a multifunctional cytokine, produced in vertebrates, mainly by activated macrophages. In vitro, it has several biological effects, including killing of transformed cells and antiparasitic effects. Moreover, TNF-α has been shown to have a lectin-like property for the oligosaccharide ligands chitobiose and Man(a1,3)-Man(a1,6)-Man(1, 2). Recently, Lucas and co-workers (3) have mapped the lectin-like domain of TNF-α and have shown that the domain exerts trypanolytic activity on salivarian trypanosomes such as *Trypanosoma brucei*. The lectin-like activity of TNF-α is functionally involved in interactions with trypanosomes and possibly also with other pathogens.

The prophenoloxidase (proPO) activating system represents an important defense mechanism in a large variety of invertebrates (4, 5). This system is based on the recognition of bacterial antigens such as lipopolysaccharide (LPS), or peptidoglycan and b-1,3-glucan, present as major components of the cell wall of yeasts and fungi (6, 7). Generally, upon the recognition of such carbohydrates proteinases cleave by limited proteolysis inactive proPO to its active state, phenoloxidase (PO). The active enzyme catalyses the o-hydroxylation of monophenols as well as the oxidation of diphenols to quinones which are subsequently polymerised non-enzymatically to melanin. Melanin and its precursors involved in the proPO activating system have cytotoxic and antimicrobial properties and participate in a wide range of other biological activities including phagocytosis or opsonization, encapsulation or nodule formation, degranulation and wound healing (8–11).

The prophenoloxidase activating system has been detected both in protostomian and deuterostomian species. Though proPO activating system is well documented in arthropods, data in other protostomian groups are more scarce. In annelids, melanization reactions and formation of "brown bodies" or nodules have been described in polychaetes and oligochaetes (12–16). However, biochemical detection of PO activity was so far restricted to a few species with rather controversial results. While Smith and Söderhäll (17) failed to detect proPO system in the polychaete *Aphrodite aculeata* and *Arenicola marina*, Fischer (18), Valembois et al. (19), and Porchet-Hennerè and Vernet (15) have evidenced PO activity in *Lumbricus terrestris, Eisenia foetida andrei* and *Nereis diversicolor* respectively. More recently, using L-DOPA as substrate, a 30 kDa protein responsible for PO activity was identified in the coelomic fluid of *Lumbricus rubellus*(20). A report showing that the oxidative activity of the coelomic fluid of earthworms towards L-DOPA in vitro is not affected by trypsin but completely blocked by subtilisin reflects the importance of a correct proteolytic digestion as an initial step for inactive proPO activation (19).

Since the factor which recognizes microbial carbohydrates and triggers the proPO system has not yet been described in annelids (4, 5), investigations were initiated to identify such a molecule in the coelomic fluid (CF) of *E. Foetida*. Surprisingly, it is shown in this invention that a previously described 42 kDa cytolytic protein named CCF-1 (Coelomic Cytolytic Factor 1) (21) binds LPS and b-1,3 glucan and that the same protein is also responsible for the trypanolytic activity of the coelomic fluid. By combining the glucan and LPS binding capacity with the cytolytic and trypanolytic activity, the invertebrate factor resembles the vertebrate compound TNF-α and can therefore be considered as a primitive type of cytokine, which may be useful as an alternative for TNF-α. This idea is supported by the fact that an anti-TNF monoclonal antibody (anti-TNF/TIP) crossreacts with CCF-1, whereas an anti-CCF-1 monoclonal antibody (12C9) crossreacts with TNF-α. Moreover, in *E. foetida*, CCF-1 levels are increased after LPS treatment, which ressembles the TNF induction by LPS, noticed in vertebrates. Apart from the above described characteristics, it is shown that CCF-1 also participates in the proPO cascade of the coelomic fluid of *Eisenia foetida*.

Even more surprisingly, the cytolytic, trypanolytic and glucan-binding characteristics of the protein can be attributed to a small domain of 13 amino acids as depicted in SEQ ID NO:1. Moreover, this isolated peptide of 13 amino acids shows biological activity. The sequence of this peptide, however, is completely different from the TIP region of TNF-α, although it shares some functional characteristics.

BRIEF SUMMARY OF THE INVENTION

It is an object of the current invention to provide new *Eisenia foetida* polypeptides and their corresponding nucleic acids which can be used in tumour therapy, microbial infection, inflammation or immunology.

It is another object of the invention to provide a nucleic acid coding for the peptide or polypeptide chains of biologically pure, active recombinant peptides which enable their preparation on large scale. When this nucleic acid encoding for the (poly)peptide is operably linked to an appropriate control sequence—such as a promoter—several host organisms, such as *E. coli, Bacillus* sp., *Streptomyces* sp., yeast, fungi, insect cells, plant cells or mammalian cells can be used for the production of the recombinant protein. Alternatively, the peptides may be produced by chemical synthesis.

(000A) Inhibition of rCCF-1-mediated trypanolytic activity by anti-CCF-1 and anti-TNF/TIP monoclonal antibodies, tested on *T. brucei*.

Inhibition of rCCF-1-mediated trypanolytic activity by N,N'-diacetylchitobiose, as tested on *T. brucei*.

Figure 4:
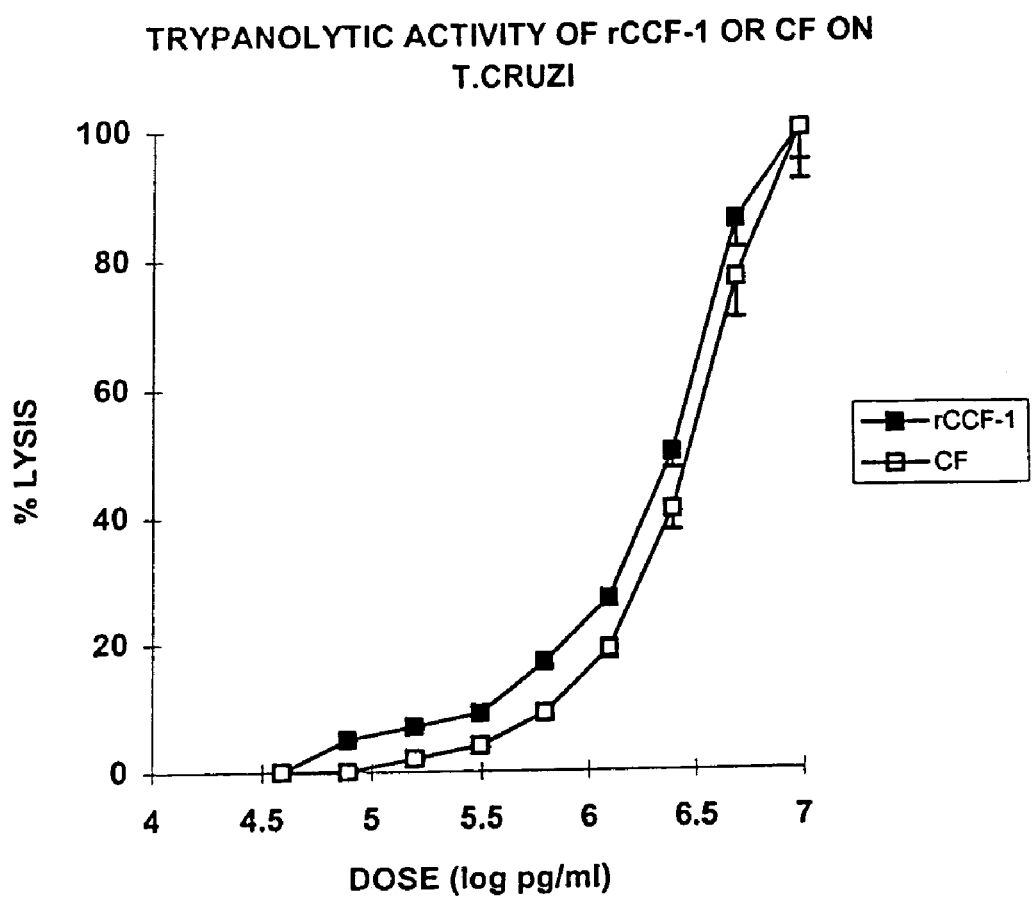

FIG. 4: Trypanolytic activity of rCCF-1 and CF on *T. cruzi*.

Figure 5:
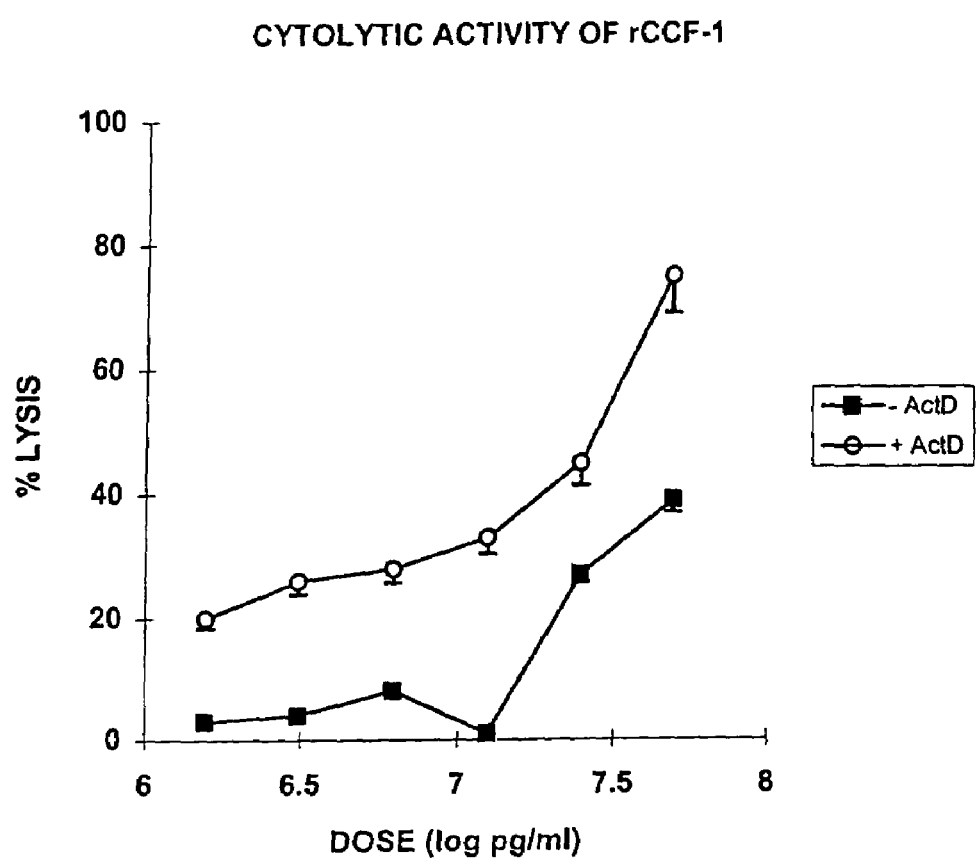

FIG. 5: Cytolytic activity of rCCF-1, as measured on L929 cells, in presence and absence of Actinomycin D (10 μg/ml)

Figure 6:
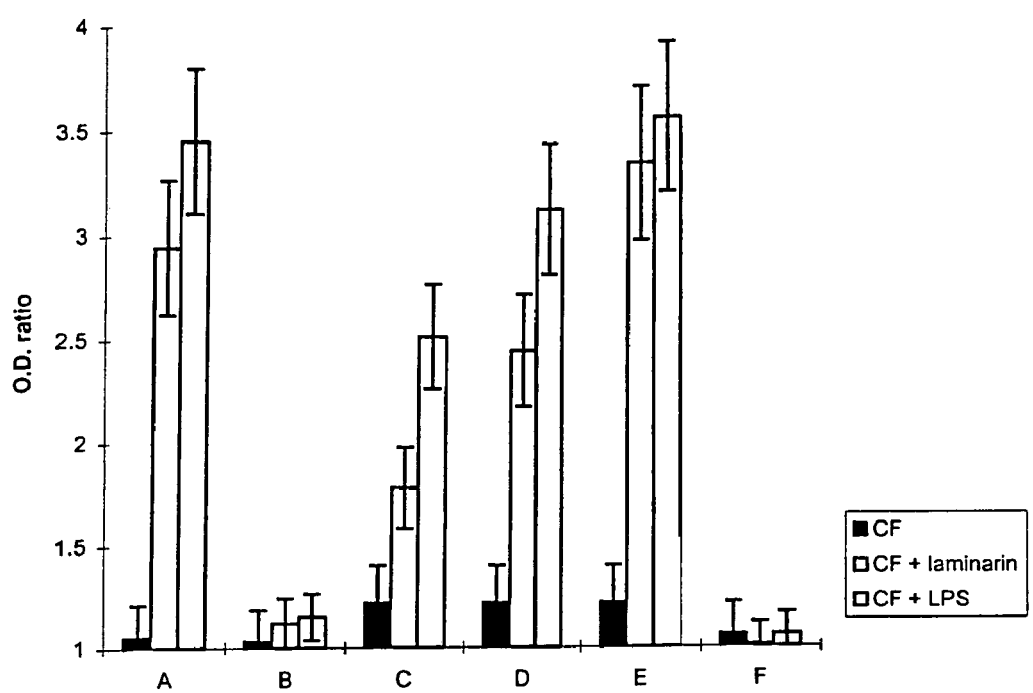

FIG. 6: Involvement of CCF-1 in the activation of PO. Level of L-DOPA oxidation, assessed after 6 hrs of incubation, is expressed as the ratio+standard deviation of OD of the sample without and with proteinase inhibitor.
(A) entire coelomic fluid
(B) CCF-1-depleted coelomic fluid by pre-incubation on anti-CCF-1 immunoaffinity column
(C) CCF-1 depleted coelomic fluid supplemented with 0.5 μg/ml rCCF-1
(D) as (C), but with 1 μg/ml rCCF-1
(E) as (C), but with 2 μg/ml rCCF-1
(F) CCF-1 depleted coelomic fluid supplemented with 2 μg/ml bovine serum albumin Laminarin or LPS were given at 2 μg/ml or 1 μg/ml respectively.

DETAILED DESCRIPTION OF THE INVENTION

A peptide or polypeptide according to this invention is characterized by the fact that it contains at least the 13 amino acids as depicted in SEQ ID NO:1 and preferably comprises at least 9 contiguous amino acids of said SEQ ID NO:1.

To the scope of the invention also relates the polypeptide of SEQ ID NO:3 or functional parts thereof.

According to another embodiment of the invention, the above defined peptides or polypeptides are exerting a trypanocidal or trypanolytical activity on *T. brucei* and/or *T. cruzi*, alone or preferably in combination with one of the following characteristics:

exerting cytolytical activity
exhibiting a b-1,3 glucan binding capacity and/or a LPS binding capacity.
exerting opsonizing and/or hemolytic activity
participating in the proPO cascade of *E. foetida*.

Accordingly another embodiment of the invention is the use of a peptide or polypeptide comprising at least 9 contiguous amino acids of SEQ ID NO:1, such as e.g. the polypeptide given by SEQ ID NO:3 for the manufacturing of a medicament to treat trypanosomal infection, bacterial infection or cancer. For the treatment of cancer, the peptide or polypeptide can be linked to a tumour specific antibody that directs the molecule to the tumor where the (poly) peptide can exert its cytolytical activity.

Another embodiment of the invention is the use of a peptide or polypeptide comprising at least 9 contiguous amino acids of SEQ ID NO:1 for the preparation of a medicament to treat a trypanosomal infection, a bacterial infection or cancer.

The invention thus relates to a DNA sequence encoding an *Eisenia foetida* protein or polypeptide or encoding an immunologically active and/or functional fragment thereof selected from the group consisting of (a) DNA sequences comprising a nucleotide sequence encoding a protein or peptide comprising the amino acid sequence as given in SEQ ID NO:1 or 3;
(b) DNA sequences comprising a nucleotide sequence as given in SEQ ID NO:2;
(c) DNA sequences hybridizing with the complementary strand of a DNA sequence as defined in (a) or (b) and encoding an amino acid sequence which is at least 80% identical to the amino acid sequence encoded by the DNA sequence of (a) or (b);
(d) DNA sequences the nucleotide sequence of which is degenerated as a result of the genetic code to a nucleotide sequence of a DNA sequence as defined in any one of (a) to (c); and
(e) DNA sequences encoding a fragment of a protein encoded by a DNA sequence of any one of (a) to (d).

The present invention also relates to vectors, particularly plasmids, cosmids, viruses, bacteriophages and other vectors used conventionally in genetic engineering that contain a nucleic acid molecule alternatively called nucleic acid sequence or DNA sequence according to the invention. Methods which are well known to those skilled in the art can be used to construct various plasmids and vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the nucleic acid molecules and vectors of the invention can be reconstituted into liposomes for delivery to target cells.

In a preferred embodiment the nucleic acid molecule present in the vector is linked to (a) control sequence(s) which allow the expression of the nucleic acid molecule in prokaryotic and/or eukaryotic cells.

The term "control sequence" refers to regulatory DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is used.

Thus, the vector of the invention is preferably an expression vector. An "expression vector" is a construct that can be used to transform a selected host cell and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotic and/or eukaryotic cells are well known to those skilled in the art. In the case of eukaryotic cells they comprise normally promoters ensuring initiation of transcription and optionally poly-A signals ensuring termination of transcription and stabilization of the transcript. Additional regulatory elements may include transcriptional as well as translational enhancers. Possible regulatory elements permitting expression in prokaryotic host cells comprise, e.g., the $P_L$, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Advantageously, the above-described vectors of the invention comprises a selectable and/or scorable marker. Selectable marker genes are well known to those skilled in the art and comprise, for example, npt which confers resistance to the aminoglycosides neomycin, kanamycin and paromycin (Herrera-Estrella, EMBO J. 2 (1983), 987–995) and hygro, which confers resistance to hygromycin (Marsh, Gene 32 (1984), 481–485).

Useful scorable marker are also known to those skilled in the art and are commercially available. Advantageously, said marker is a gene encoding luciferase (Giacomin, Pl. Sci. 116 (1996), 59–72; Scikantha, J. Bact. 178 (1996), 121), green fluorescent protein (Gerdes, FEBS Lett. 389 (1996), 44–47) or β-glucuronidase (Jefferson, EMBO J. 6 (1987), 3901–3907). This embodiment is particularly useful for simple and rapid screening of cells, tissues and organisms containing a vector of the invention.

The present invention furthermore relates to host cells comprising a vector as described above or a nucleic acid molecule according to the invention wherein the nucleic acid molecule is foreign to the host cell.

By "foreign" it is meant that the nucleic acid molecule is either heterologous with respect to the host cell, this means derived from a cell or organism with a different genomic background, or is homologous with respect to the host cell but located in a different genomic environment than the naturally occurring counterpart of said nucleic acid molecule. This means that, if the nucleic acid molecule is homologous with respect to the host cell, it is not located in its natural location in the genome of said host cell, in particular it is surrounded by different genes. In this case the nucleic acid molecule may be either under the control of its own promoter or under the control of a heterologous promoter. The vector or nucleic acid molecule according to the invention which is present in the host cell may either be integrated into the genome of the host cell or it may be maintained in some form extrachromosomally.

The host cell can be any prokaryotic or eukaryotic cell, such as bacterial, insect, fungal, plant or animal cells. Preferred fungal cells are, for example, those of the genus *Saccharomyces*, in particular those of the species *S. cerevisiae*.

Another subject of the invention is a method for the preparation of an *Eisenia foetida* protein which comprises the cultivation of host cells according to the invention which, due to the presence of a vector or a nucleic acid molecule according to the invention, are able to express such a protein, under conditions which allow expression of the protein and recovering of the so-produced protein from the culture.

The term "expression" means the production of a protein or nucleotide sequence in the cell. However, said term also includes expression of the protein in a cell-free system. It includes transcription into an RNA product, post-transcriptional modification and/or translation to a protein product or polypeptide from a DNA encoding that product, as well as possible post-translational modifications. Depending on the specific constructs and conditions used, the protein may be recovered from the cells, from the culture medium or from both. For the person skilled in the art it is well known that it is not only possible to express a native protein but also to express the protein as fusion polypeptides or to add signal sequences directing the protein to specific compartments of the host cell, e.g., ensuring secretion of the peptide into the culture medium, etc. Furthermore, such a protein and fragments thereof can be chemically synthesized and/or modified according to standard methods.

The terms "protein" and "(poly)peptide" used in this application are interchangeable. "(Poly)peptide" refers to a polymer of amino acids (amino acid sequence) and does not refer to a specific length of the molecule. Thus peptides and oligopeptides are included within the definition of polypeptide. This term does also refer to or include post-translational modifications of the polypeptide, for example, glycosylations, acetylations, phosphorylations and the like. Included within the definition are, for example, polypeptides containing one or more analogs of an amino acid (including, for example, unnatural amino acids, etc.), polypeptides with substituted linkages, as well as other modifications known in the art, both naturally occurring and non-naturally occurring.

The present invention furthermore relates to proteins encoded by the nucleic acid molecules according to the invention or produced or obtained by the above-described methods, and to functional and/or immunologically active fragments of such proteins. The proteins and polypeptides of the present invention are not necessarily translated from a designated nucleic acid sequence; the polypeptides may be generated in any manner, including for example, chemical synthesis, or expression of a recombinant expression system, or isolation from a suitable viral system. The polypeptides may include one or more analogs of amino acids, phosphorylated amino acids or unnatural amino acids. Methods of inserting analogs of amino acids into a sequence are known in the art. The polypeptides may also include one or more labels, which are known to those skilled in the art. In this context, it is also understood that the proteins according to the invention may be further modified by conventional methods known in the art. By providing the proteins according to the present invention it is also possible to determine fragments which retain biological activity, namely the mature, processed form. This allows the construction of chimeric proteins and peptides comprising an amino sequence derived from the protein of the invention, which is crucial for its binding activity and other functional amino acid sequences. The other functional amino acid sequences may be either physically linked by, e.g., chemical means to the proteins of the invention or may be fused by recombinant DNA techniques well known in the art.

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to, while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 30 amino acids. It is usually desirable to select sequences of at least about 10, 12 or 15 amino acids, up to a maximum of about 20 or 25 amino acids. Specifically in this context is referred to SEQ ID NO:1 comprising 13 amino acids showing the essential cytolytic, trypanolytic and glucan-binding characteristics comparable to the whole protein.

Furthermore, folding simulations and computer redesign of structural motifs of the protein of the invention can be performed using appropriate computer programs (Olszewski, Proteins 25 (1996), 286–299; Hoffman, Comput. Appl. Biosci. 11 (1995), 675–679). Computer modeling of protein folding can be used for the conformational and energetic analysis of detailed peptide and protein models (Monge, J. Mol. Biol. 247 (1995), 995–1012; Renouf, Adv. Exp. Med. Biol. 376 (1995), 37–45). In particular, the appropriate programs can be used for the identification of interactive sites of the protein according to the invention, its receptor, its ligand or other interacting proteins by computer assistant searches for complementary peptide sequences (Fassina, Immunomethods 5 (1994), 114–120). Further appropriate computer systems for the design of protein and peptides are described in the prior art, for example in Berry, Biochem. Soc. Trans. 22 (1994), 1033–1036; Wodak, Ann. N.Y. Acad. Sci. 501 (1987), 1–13; Pabo, Biochemistry 25 (1986), 5987–5991. The results obtained from the above-described computer analysis can be used for, e.g., the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218–33224). For example, incorporation of easily available achiral-amino acid residues into a protein of the invention or a fragment thereof results in the substitution of amide bonds by polymethylene units of an aliphatic chain, thereby providing a convenient strategy for constructing a peptidomimetic (Banerjee, Biopolymers 39 (1996), 769–777). Superactive peptidomimetic analogues of small peptide hormones in other systems are described in the prior art (Zhang, Biochem. Biophys. Res. Commun. 224 (1996), 327–331). Appropriate peptidomimetics of the protein of the present invention can also be identified by the synthesis of peptidomimetic combinatorial libraries through successive amide alkylation and testing the resulting compounds, e.g., for their binding and immunological properties. Methods for the generation and use of peptidomimetic combinatorial libraries are described in the prior art, for example in Ostresh, Methods in Enzymology 267 (1996),220–234 and Dorner, Bioorg. Med. Chem. 4 (1996), 709–715.

Furthermore, a three-dimensional and/or crystallographic structure of the protein of the invention can be used for the design of peptidomimetic inhibitors of the biological activity of the protein of the invention (Rose, Biochemistry 35 (1996), 12933–12944; Rutenber, Bioorg. Med. Chem. 4 (1996), 1545–1558).

Furthermore, the present invention relates to antibodies specifically recognizing an *Eisenia foetida* protein according to the invention or parts, i.e. specific fragments or epitopes, of such a protein. The antibodies of the invention can be used to identify and isolate other *Eisenia foetida* proteins and genes in any organism. These antibodies can be monoclonal antibodies, polyclonal antibodies or synthetic antibodies as well as fragments of antibodies, such as Fab, Fv or scFv fragments etc. Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. These antibodies can be used, for example, for the immunoprecipitation and immunolocalization of proteins according to the invention as well as for the monitoring of the synthesis of such proteins, for example, in recombinant organisms, and for the identification of compounds interacting with the protein according to the invention. For example, surface plasmon resonance as employed in the BIAcore system can be used to increase the efficiency of phage antibodies selections, yielding a high increment of affinity from a single library of phage antibodies which bind to an epitope of the protein of the invention (Schier, Human Antibodies Hybridomas 7 (1996), 97–105; Malmborg, J. Immunol. Methods 183 (1995),7–13). In many cases, the binding phenomena of antibodies to antigens is equivalent to other ligand/anti-ligand binding.

EXAMPLES

1. Purification and Partial Sequencing of CCF-1

CCF-1 was prepared and purified as described earlier (21). Analysis on 2 dimensional polyacryl amide gel electrophoresis (PAGE) confirmed the homogeneity of the CCF-1 preparation since a single spot was detected. A bulk preparation of immunoaffinity purified CCF-1 was separated on a preparative SDS-PAGE, blotted on PVDF problott and stained with amido black. $\frac{1}{10}^{th}$ of the amount of the immobilised protein was N-terminal sequenced for 30 cycles. The N-terminal amino acid sequence of 30 residues is shown in Table 1. The remaining part of the CCF-1 containing PVDF band was used for internal sequence determination. To this end, tryptic digestion was performed according to the method of Fernandez et al. (22). After cleavage, the released peptides were separated on a reverse phase column (Vydac C4, 2.1×250 mm) and eluted with a linear gradient (0% to 70%) of acetonitrile in 0.1% trifluoroacetic acid. The column outlet was directly connected to a 1000 S diode assay detector (Applied Biosystems) and the most prominent peaks were used for amino acid sequencing. Purified peptides were sequenced using a pulsed-liquid model 477A sequenator (Applied Biosystems). The sequences of some of the peptides are shown in Table 1. From a number of peptide sequences degenerate PCR primers were deduced to identify CCF-1 cDNA from a cDNA library of *E. foetida*.

2. Trypanolytic Activity of CCF-1

Coelomic Fluid Collection

Coelomic fluid from adults *Eisenia foetida* earthworms was obtained by puncturing the coelomic cavity with a glass micropipette in presence of protease inhibitor (Pefabloc, Boehringer, 10 mM). The pooled suspension was centrifuged (100×g, 10 min), and the cell-free coelomic fluid after re-centrifugation (3000×g, 10 min) was stored at −70° C. until used.

Monoclonal Antibodies (mAb's)

Generation of anti-CCF-1 monoclonal antibodies (12C9) was previously reported (21, 24). Isotype matched monoclonal antibody 15D3 (IgG1) against *Bandeiraea simplicifolia* B4 isolectin was prepared using standard procedures and used as control in trypanolysis assays.

Parasites

Pleiomorphic and monomorphic *Trypanosoma brucei* AnTat 1.1E clone were provided by Dr N. Van Meirvenne (Institute of Tropical Medicine, Antwerp, Belgium).

Trypanolytic Assay

Purified parasites were resuspended at 4×10⁶/ml PSG (PBS, consisting of 2.13 g NaCl, 8.45 g $Na_2HPO_4$ and 0.43 g $NaH_2PO_4$ per liter, supplemented with 1% glucose). 100 ml of suspension were mixed with 100 ml of different concentrations of CF, CCF-1 or TNF-α in 96-well culture plate. Quantification of the trypanolysis was based on the determination of parasite viability using Ethidium homodimer (EthD-1, Molecular Probes). EthD-1 is excluded by intact plasma membrane of live parasites. However, it enters the cells with damaged membrane and undergoes enhancement of fluorescence on binding nucleic acids, thereby producing a bright red fluorescence in dead cells. Briefly, after 4.5 hrs incubation at 30° C., 25 ml of 4.5 mM EthD-1 was added to the wells. The mean fluorescence intensity of triplicate cultures (±SD) was recorded 30 min later in a cytofluorimeter (Cytofluor II, PerSeptive Biosystems) using excitation/emission filters at 530±25/645±40 nm. A set of control was included in each experiments: (A) a parasite-free control to account for possible background fluorescence (B) a control of 100% lysis, prepared by treating the parasites with 10 ml 2% saponin for about 10 min before adding EthD-1 (C) a control in which the trypanolytic component was replaced by PSG was considered as 0% lysis. (B) and (C) were used to build a standard curve and the % lysis in test samples was estimated by linear regression. In some assays parasite lysis was assessed by light microscopy counting the remaining parasites. Background lysis, i.e. lysis of trypanosomes within 5 hrs incubation at 30° C. in absence of lytic molecules, never exceeded 5–10%.

For inhibition experiments CCF-1 or TNF-α were pre-incubated 1 hr at 30° C. with 10 mg/ml of antibodies (anti-CCF1, anti-TIP or irrelevant mAb) or sugars (chitobiose, cellobiose, Sigma). All experiments were repeated at least 3 times.

Lysis of African Trypanosomes

CF of *E. foetida* exerts a trypanolytic activity on *T. brucei* parasites not being due to proteolysis because all experiments were performed in the presence of a non-toxic serine proteinase inhibitor. Immunoaffinity purified CCF-1 exerts also a trypanolytic activity, 1000-times higher as compared to the total CF indicating an efficient enrichment. The trypanolytic activity of total CF as well as of CCF-1 is completly inhibited by the neutralizing antibody mAb 12C9 (21) indicating that CCF-1 accounts for the total trypanolytic activity of CF (Table 2).

Since the trypanolytic activity of TNF-α is mediated by a lectin-like domain, it was tested whether CCF-1 exhibits similar features. N,N'-diacetylchitobiose, a potent inhibitor of the trypanolytic activity of TNF-α was found to inhibit also the trypanolytic activity of CCF-1. In contrast, cellobiose, that does not influence the trypanolytic activity of TNF-α, does not influence the trypanolytic activity of CCF-1 either. These results indicate that the CCF-1/trypanosome interaction involves a lectin-like activity. The lectin-like activity of TNF-α is mediated by a distinct domain of the molecule encompassing the amino acid sequence (SEQ ID NO:15) $T^{104}PEGAE^{109}$, designated as the TIP region of TNF-α(3). Since anti-TIP antibodies strongly inhibit the trypanolytic but not the cytolytic activity of TNF-α, the influence of such antibodies (polyclonal and monoclonal) was tested on the trypanolytic activity of CCF-1. According to these results, anti-TIP antibodies inhibit potently this activity (Table 3). Another monoclonal anti-TNF-α antibody (1F3F3) that neutralizes potently the cytolytic (3) but weakly the trypanolytic activity of TNF-α does not interfere with CCF-1-mediated trypanolysis. These results suggest that CCF-1 and TNF-α share a similar region that mediates with interaction trypanosomes. This possibility was further on substantiated by following observations: (1) the neutralizing anti-CCF-1 mAb 12C9 inhibits the trypanocidal activity of TNF-α (Table 3), (2) monoclonal anti-TIP antibodies cross-react with CCF-1 in western blot and conversely the anti-CCF-1 mAb 12C9 binds on immobilized TNF-α, (3) both CCF-1 and TNF-α bind to immobilized chitobiose.

Lysis of American Trypanosomes

It has been demonstrated that TNF-α exerts also trypanolytic activity on the American trypanosome *T. cruzi*. This trypanolytic activity can be inhibited by N,N'-diacetylchitobiose and by anti-TNF/TIP antibodies but not by the anti-TNF-α mAb 1F3F3 that neutralizes the cytolytic effects of TNF-α.

In view of these results, we have tested whether CF is trypanolytic for *T. cruzi*. The results are summarized in Table 4. CF contains components that lyse *T. cruzi* and this lytic activity is substantially decreased by the neutralizing anti-CCF-1 mAb 12C9 and by N,N'-diacetylchitobiose, but not by cellobiose. Hence the results indicate that CCF-1 is the major *T. cruzi* trypanolytic molecule of total CF and that this activity is again mediated via a lectin-like interaction similar to that one of TNF-α. Interestingly the *T. cruzi* trypanolytic activity of both TNF-α and CCF-1 could only be recorded on the trypomastigote but not the epimastigote forms of the parasite indicating that the susceptibility towards the lytic activity of TNF-α and CCF-1 is developmentally regulated.

3. Cytolytic Activity of CCF-1

To test whether the cytolytic activity of CCF-1 is mediated by a similar or a different domain as that one utilized for the trypanolytic activity, CCF-1 was preincubated with N,N'-diacetylchitobiose or anti-TNF/TIP antibodies and tested in the L-929 lysis assay (21). The results are shown in Table 5. These results clearly demonstrate that the interaction of CCF-1 with L-929 cells is completely inhibited by treatment with N,N'-diacetylchitobiose and anti-TNF/TIP antibodies. This is in sharp contrast to the cytolytic activity of TNF-α that is not influenced by anti-TNF/TIP antibodies nor by N,N'-diacetylchitobiose. Hence, CCF-1 utilizes its lectin-like domain to interact with trypanosomes and mammalian (L-929) cells and this interaction leads to cellular lysis.

4. Identification of the Trypanolytic Domain of CCF-1

Figure 1:
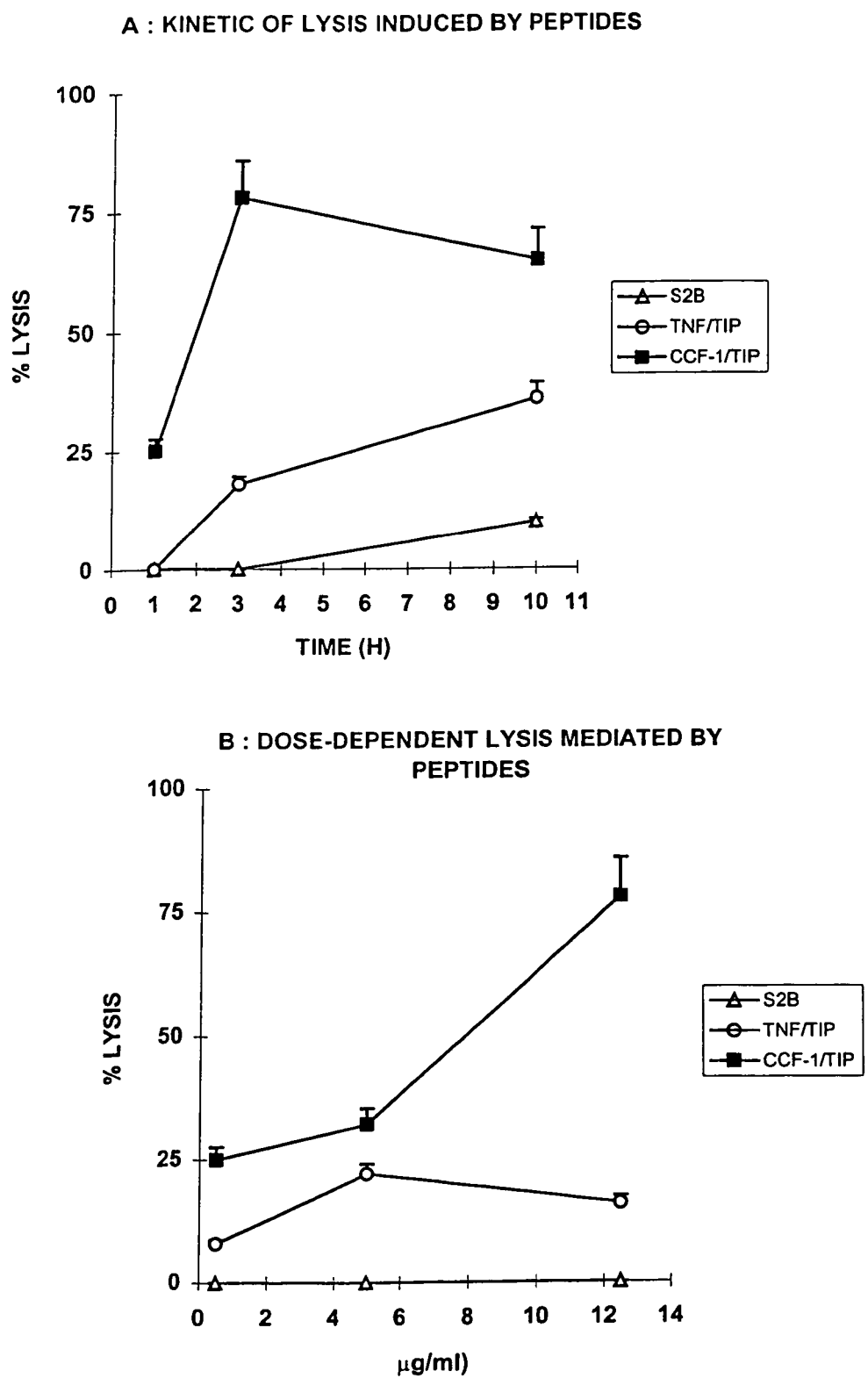
FIGS. 1A and 1B: Trypanolytic activity of peptides (00JJ) Trypanolysis in function of the time (0.0125 mg/ml peptide) (00KK) Trypanolysis (after 3 hours) in function of the concentration. S2B is a biotinylated, irrelevant peptide.

The separated peptides obtained from HPLC purification of the tryptic digest of CCF-1 were analyzed for reactivity with the anti-CCF-1 mAb via a dot spot assay. One peptide scored weakly positive with the 12C9 mAb and this peptide was sequenced. The obtained sequence is shown in SEQ ID NO:1. This peptide (termed CCF-1/TIP), which is clearly different from the TNF/TIP, was tested in trypanolysis assay and was found to be trypanolytic in a time- and dose-dependent way (FIG. 1). Furthermore, the CCF-1/TIP was reproducibly more trypanolytic than the TNF/TIP peptide, while irrelevant peptides were not or marginally trypanolytic (FIG. 1).

Profile analysis of the CCF-1/TIP sequence against the Swiss-prot database revealed that the CCF-1/TIF peptide contains a pattern that is unique for glycosyl hydrolases.

5. Cloning and Expression of CCF-1

Molecular Cloning

RNA Extraction

Earthworms were taken from compost and put on filter paper soaked with PBS for four days in order to clean their gut. After two days, Penicillin/Streptomycin (100U/100 µg/ml) were added to decrease the amount of micro-organisms in the worms and the worms were treated with LPS, a known inducer of CCF-1 synthesis. Three worms were frozen in liquid nitrogen, ground to powder and total RNA was prepared as described by Chomczynski and Sacchi (23). Poly A+RNA was isolated from the total RNA using the polyAtract system (Promega). Biotinylated-Oligo(dT) was added to the total RNA and allowed to bind the poly A+RNA. Using streptavidin-paramagnetic beads, the oligo (dT)-mRNA hybrids were captured and finally the mRNA was eluted. The mRNA isolated yielded 8 µg mRNA in 250 µl. After analysis on agarose gel, a smear of mRNA was observed and the rRNA was almost completely removed.

cDNA Library Construction cDNA was synthesized using a cDNA synthesis module (Amersham).

To make a cDNA library, the lambda zap II vector of Stratagene was used. Before inserting the cDNA in the lambda vector, EcoR I adaptors were ligated onto the ends of the cDNA. The adapted cDNA was size fractionated, phosphorylated and ligated in the lambda arms. The recombinant lambda DNA was packaged in vitro with Gigapack II Gold Packaging extracts (Stratagene). *E. coli* (strain XL1-Blue MRF', Stratagene) was infected with the phage suspension for amplification and determination of the phage titer.

Isolation of CCF-1 cDNA

Degenerate primers were deduced from a number of native earthworm CCF-1 peptide sequences in order to identify the CCF-1 cDNA from the *E. foetida* library. Combination of the following primers SEQ ID NO:4 (5'TI-ACIGAITGGGAICAA/GTAT/CATIGTITGGCA3' and SEQ ID NO:5 5'AAIGTITGIAAITTG/ATCICCG/ATAG/ATTCCA3') resulted in a specific PCR fragment. A DIG labelled PCR product (DIG labelling mix, Boehringer, Mannheim) was subsequently used as a CCF-1 specific probe in plaque hybridization. Positive plaques were isolated and the presence of CCF-1 cDNA was confirmed with PCR. In order to obtain pBluescript phagemids in vivo excision was performed according to Stratagene's recommendations.

Sequence Analysis of the CCF-1 cDNA

Since the 2500 bp EcoR I insert was too large to be sequenced in one run and since no information was available on the DNA sequence of the insert, deletions were made of the clone. With a Erase-a-base system (Promega) a series of deletions of the EcoR I insert of the pBluescript vector were made in which the insert was each time 250 bp smaller. Using these deletions it was possible to sequence the 2500 bp EcoR I insert of the pBluescript vector.

Analysis of CCF-1 cDNA

The sequencing revealed that the EcoR I insert was 2682 bp in length. In the insert two open reading frames (ORF)

were recognized. One ORF showed a strong homology with cDNA of the Myosin essential light chain of the earthworm *Lumbricus terrestris*. In the second ORF, all identified sequences, including the CCF-1/TIP sequence, of the natural CCF-1 of *E. foetida* were present. These results indicate that the second ORF is the complete cDNA of CCF-1. Further analysis of the CCF-1 cDNA showed that the full length cDNA was isolated with a length of 1155 bp, starting with an ATG initiation codon and ending with a TGA stop codon (SEQ ID NO:2). The deduced amino acid sequence contains an eukaryotic signal sequence of 17 amino acids, indicating that the mature CCF-1 starts at amino acid 18. The deduced amino acid sequence contains 3 cysteins, possibly forming one sulphur bridge. There are no N-glycosylation sites present, excluding N-glycosylation of the protein. Since the molecular weight of the natural CCF-1 and of the deduced amino acid sequence are similar, there are probably no O-glycosylations present.

Expression of Recombinant CCF-1

Construction of the pIGRI-CCF-1 and pIGRHISA-CCF-1 Vector

The c-DNA sequence encoding for mature CCF-1 (mCCF1) was amplified by PCR using PWO polymerase (Boehringer Mannheim) and the pBluescript phagemid as template. The primers were designed so that after PCR, the m-CCF-1 cDNA contained BamH I/ Nsi I sites at the 5' end SEQ ID NO:6 (GG GGATCCATGCATTCACCGACTGGGATCAATATCAC) and a Sal I site at the 3'end SEQ ID NO:7 (CC GTCGACTCAGTTGCGCTTGTAGACTCG). Hence, after cutting the PCR product with Nsi I and blunting the sticky ends, the first codon of the mCCF-1 was blunt-end available for ligation.

The BamH I-Sal I fragment was subcloned in pBluescript (pBSmCCF-1) and checked by sequencing. A Nsi I blunted -Sal I fragment containing the mCCF-1 cDNA from pBSm-CCF-1 was cloned into pIGRI2 (resulting in pIGRI-CCF-1) and pIGRHISA (resulting in pIGRHISA-CCF-1). pIGRI2 is a vector for intracellular expression of mature proteins and pIGRHISA is a vector for expression of proteins including a His-tag. In the latter vector, the mCCF-1 cDNA sequence is preceded by an amino-terminal His-tag and an enterokinase cleavage site. After transformation in the *E. coli* strain MC1061 pAcI the clones were ready for induction.

Induction of Recombinant CCF-1 Protein (rCCF-1)

Since CCF-1 in both constructs is under control of the $P_L$ promoter, cultures were grown at 32° C. and induced at 42° C. at an $OD_{600}$ of 0.7. Total cell lysates showed an extra band after induction of the cultures for both the mature and the His-tag recombinant protein. The band after induction of pIGRI-CCF-1 had a size of approximately 42 kDa and the band after induction of pIGRHIA-CCF-1 had a size of approximately 44 kDa. High expression of recombinant protein was obtained and both bands were the most prominent ones of the total cell lysates.

In order to prove that the induced *E coli* proteins of 42 or 44 kDa were indeed CCF-1, a western blot was performed using mAb 12C9 and mAb against TNF/TIP. Both recombinant proteins showed a clear band on western blot incubated with 12C9 mAb as well as with anti-TNF/TIP mAb. Moreover, the binding capacity towards laminarin, LPS and N,N'-diacetylchitobiose of the proteins, produced by *E coli*, is comparable with the capacity of natural CCF-1. These data clearly show that the induced protein (with and without His-tag) is CCF-1.

Purification of rCCF-1

One liter of pIGRHISA-CCF-1 transformed bacterial culture was resuspended in PBS and sonicated. After sonication, the pellet of *E. coli* transformed with rCCF-1 cDNA cloned into pIGRHISA plasmid was solubilized in urea (8 M in 20 mM Tris pH 8.5–50 mM NaCl), applied on 2.5 ml Ni-NTA agarose resin (Qiagen) and renatured by a linear decreasing gradient of urea while rCCF-1 was bound on the column. Elutions were performed by imidazole (300 mM in 20 mM Tris pH 8.5–50 mM NaCl) and imidazole was removed by extensive dialysis against PBS pH 8.0. rCCF-1 was further purified to homogeneity by immunoaffinity on anti-CCF-1 12C9 or anti-TIP 24C11 monoclonal antibody columns.

6. Biological Activity of rCCF-1

Trypanolytic Activity

Figure 2:
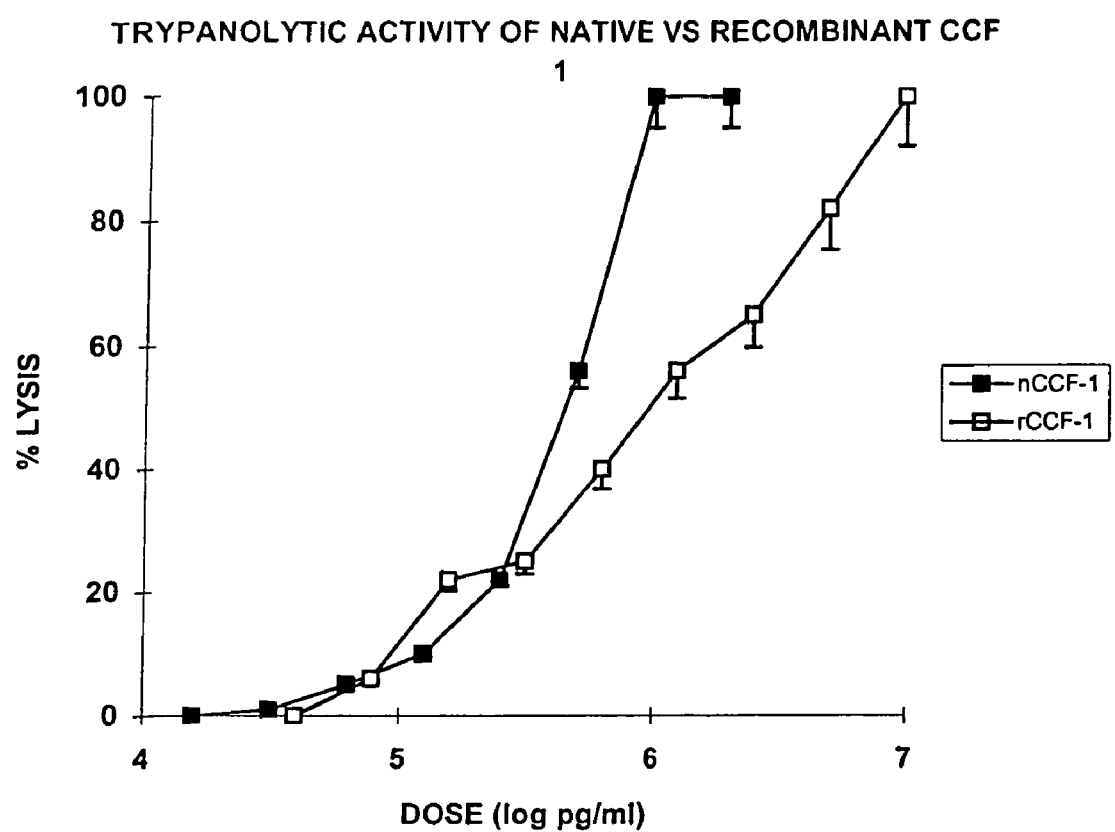
FIG. 2: Trypanolytic activity of purified natural CCF-1 (nCCF-1) versus recombinant CCF-1 (rCCF-1), tested on *T. brucei*.
Figure 3:
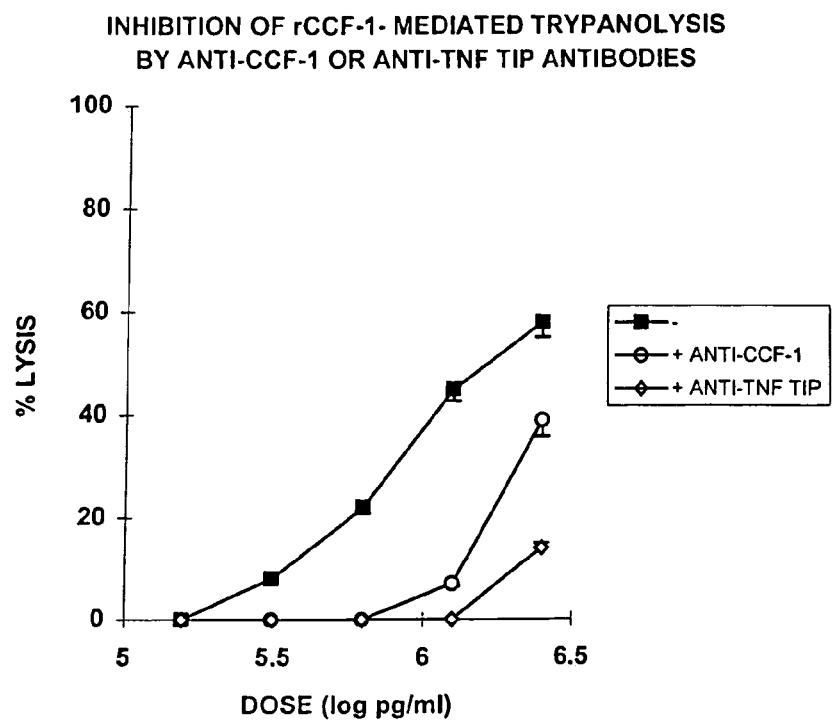
FIGS. 3A and 3B.
Figure 3:
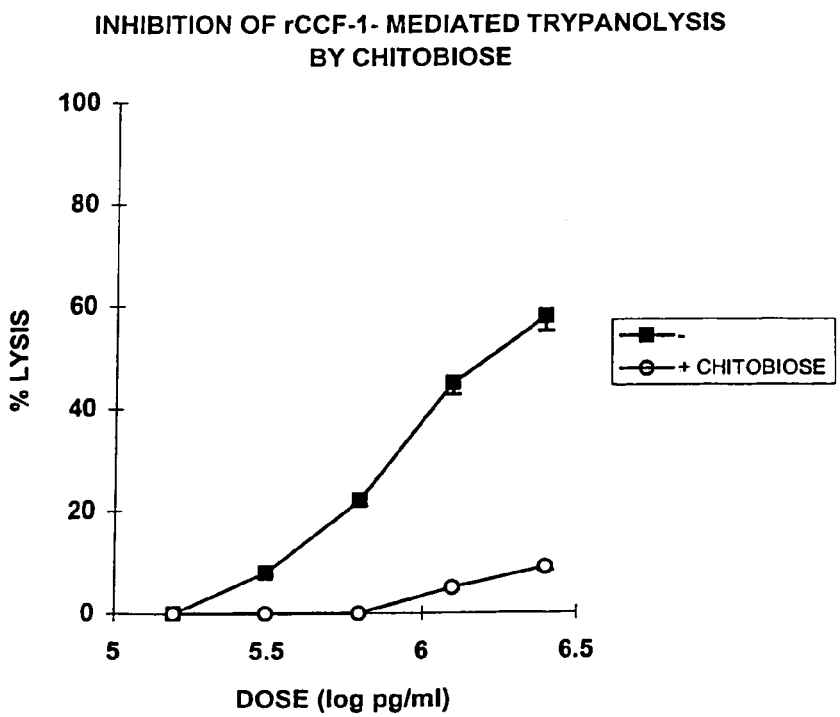

The trypanolytic activity was determined as described above under point 2. rCCF-1 is trypanolytic for the African trypanosome *T. brucei* in a dose dependent manner (FIG. 2). The trypanolytic activity of rCCF-1 can be inhibited by anti-CCF-1 and anti-TNF/TIP mAb's (FIG. 3A). Furthermore N,N'-diacteylchitobiose inhibits potently trypanolytic activity of rCCF-1 (FIG. 3B). These data corroborate the findings that CCF-1 shares a trypanolytic, lectin-like domain with TNF-α.

rCCF-1 exerts also a trypanolytic activity on the American trypanosome *T. cruzi* (FIG. 4).

Cytolytic Activity

Cytolytic activity of rCCF-1 was tested as described (21). rCCF-1 is clearly cytolytic, especially in the presence of actinomycin D, a well known enhancer of the cytolytic activity of TNF-α (FIG. 5).

Involvement in Prophenoloxidase Activation

The level of prophenoloxidase system activation was assessed according to Valembois et al. (19). Briefly, 50 μl of the coelomic fluid (without or with 1 mM Pefabloc {serine proteinase inhibitor}, Boehringer), 25 μl 0.1 M Tris pH 8 containing 50 mM $Ca^{2+}$ and 10 μl L-DOPA (3-(3,4-dihidroxylphenyl)-L-alanine {Fluka}, final concentration 1.5 mM) were incubated at room temperature for different time intervals in the absence or presence of soluble LPS from *E. coli* (Difco, 1 μg/ml) or laminarin (Sigma, 2 μg/ml). The oxidation of L-DOPA was measured at 492 nm and expressed as the ratio between the values without and with Pefabloc. To confirm the role of glucan- or LPS-binding protein in proPO activation the coelomic fluid was incubated with anti-CCF-1 (12C9) immunoaffinity column (Affi-Gel, Bio-Rad) for 1 hr at 4° C. The samples were centrifuged and the depleted coelemic fluid was used in L-DOPA oxidation test as described above. To reconstitute the proPO activating cascade, rCCF-1 (0.5, 1 and 2 μg/ml) was added to CCF-1 depleted coelomic fluid before testing L-DOPA oxidation.

In order to confirm that CCF-1 glucan- and LPS-binding protein is involved in the activation of proPO cascade, CCF-1 was removed from the entire coelomic fluid by preincubation with insoluble glucan or anti-CCF-1 antibody column. This results in a significant decrease of the oxidative activity of the coelomic fluid even in presence of laminarin or LPS (FIG. 6). The activity of the CCF-1 depleted coelomic fluid can be completely recovered by addition of rCCF-1.

7. In vivo Activity of CCF-1

CCF-1 Purification

Native CCF-1 (CCF-1) and recombinant CCF-1 (rCCF-1) were purified as described above. Both CCF-1 and rCCF-1 were finally suspended in PBS (pH8)

Parasites

Pleiomorphic and monomorphic *Trypanosoma brucei* AnTat 1.1E clone, kindly were provided by Dr N. Van Meirvenne (Institute of Tropical Medicine, Antwerp, Belgium). Female (C57B1/6×Balb/c) F1 mice (2 months old, Bantin and Kingman, North Humberside, UK) were inoculated intraperitoneally with $2\times10^3$ viable bloodstream form parasites. Animals were bled on heparin (20 U/ml) at the first peak of parasitaemia. Blood was diluted in an equal volume PSG and purified over a DE52 cellulose ion exchange chromatography column (Whatman) using PSG for equilibration and elution (25). Purified trypanosomes were subsequently washed in PSG (1000×g, 20 min).

Antibodies

Generation of anti-CCF-1 monoclonal antibodies (12C9) was previously reported (21, 24). Isotype matched monoclonal antibody 15D3 (IgG1) against *Bandeiraea simplicifolia* B4 isolectin was used as control in trypanolysis assays and during in vivo antibody treatment of *T. brucei* infected mice.

Trypanolytic Assay

The trypanolytic assay was carried out as described above.

Antibody or rCCF-1 Treatment During Trypanosome Infection

Groups of (C57B1/6×Balb/c) F1 mice received one intraperitoneal injection of 50 mg purified antibody(anti-CCF-1, anti-TIP or control mAb) or 200 mg rCCF-1 24 hr before infection with $2\times10^3$ pleomorphic AnTat 1.1 parasites. Parasitaemia was monitored by tail blood puncture every two to four days using a counting chamber. Before treatment of mice, antibodies were adsorbed on polymyxin beads (Sigma) to avoid LPS contamination. The presence of LPS in rCCF-1 preparation was excluded by E-Toxate test (Sigma).

Anti-CCF-1 Treatment Increases Parasite Load in *T.brucei*-Infected Mice.

Treatment of *T.brucei*—infected mice with TNF/TIP—specific antibody resulted in a dramatic increase in the number of parasites during the first peak of parasitaemia (24). In view of the similarity between the lectin-like domain of CCF-1 and TNF-α, we evaluated whether anti-CCF-1 monoclonal antibody treatment before *T.brucei* infection influenced the parasitaemia (Table 6). Compared to untreated or control antibody-treated mice, *T.brucei*—infected animals treated with CCF-1—specific antibodies show a substantial increase in the number of parasites in the blood (p<0.05). However the increase in parasitaemia following anti-CCF-1 treatment is lower than in anti-TNF/TIP-treated mice.

CCF-1 Treatment Impairs *T.brucei* Proliferation Within Infected Mice.

The trypanolytic activity of CCF-1 in vitro raised the possibility that CCF-1 treatment would influence the development of *T.brucei* in infected mice. As shown in Table 7, animals treated with rCCF-1 before trypanosome infection control more efficiently the replication of the parasite in the blood. The first peak of parasitaemia is reduced approximately by 30% in such mice as compared to untreated animals (p<0.05).

8. Interaction of rCCF-1 with Mammalian Cells

FACS experiments suggested that recombinant CCF-1 (rCCF-1) was bound to the 2C11–12 macrophage cell line surface.

It was also observed that 2C11–12 activated by rCCF-1 produced TNF-α (Table 8) but no other inflammatory cytokine such as IL-1 or IL-6 was produced. 2C11–12 activated with rCCF-1 did not produce nitric oxide. Recombinant CCF-1 also elicited TNF-α production by peritoneal exudate cells (PECs) from LPS-resistant mice (Table 9), excluding the possibility that TNF-α production resulted from potential contamination of rCCF-1 preparation with LPS. However, PECs required IFN-g pre-activation in order to secrete TNF-α, and produced less TNF-α as compared to 2C11–12 macrophage cell line.

These data suggest that CCF-1, an invertebrate inflammatory molecule displaying functional analogies with TNF-α, may interact with mammalian cells and induce the production of the inflammatory cytokine TNF-α.

The methods used in this example are given hereunder.

Methods

FACS Staining:

$5\times10^5$ 2C11–12 macrophage cells were incubated with 10 mg rCCF-1 (1 hr, 4° C.). After washing cells were incubated with 12C9 anti-CCF-1 monoclonal antibody (10 mg, 1 hr, 4° C.). Cells were washed and incubated with rat anti-mouse FITC-labelled antibody (ICN, 1/1000).

Cell Activation by rCCF-1:

2C11–12 macrophage cells ($5\times10^5$ cells/ml RPMI containing 10% fetal calf serum) were activated with different doses of rCCF-1. After 24 hr incubation at 37° C., TNF-α production was quantified in culture supernatants using a TNF-α-specific ELISA (Pharmingen).

PECs were collected from the peritoneal cavity of C3H/J mice (LPS resistant) using 0.34 M sucrose. After washing in RPMI containing 10% fetal calf serum, PECs ($5\times10^5$ cells/ml) were activated with rCCF-1 in absence and presence of recombinant murine IFN-g (Gibco, 10 U/ml). After 24 hr, TNF-α levels in culture supernatants were estimated as described above.

REFERENCES

1. Hession, C., et al., (1987) Science, 237, 1479–1484.
2. Sherblom, A., Deckers, J. and Muchmore, V.(1988)J. Biol. Chem., 263, 5418–5424.
3. Lucas, R., Magez, S., De Leys, R., Fransen, L., Scheerlinck, J.-O., Rampelberg, M., Sablon, E. and De Baetselier, P.(1994)Science, 263, 814–817.
4. Smith, V. J.(1996)in Advances in Comparative and Environmental Physiology, vol. 23 (Cooper, E. L., ed.), pp. 75–114, Springer-Verlag, Berlin, Heidelberg, N.Y.
5. Johansson, M. and Söderhäll, K.(1996)in Invertebrate Immunology (Rinkevich, B. and Müller, W., eds.) pp. 46–67, Springer-Verlag, Berlin, Heidelberg, N.Y.
6. Ashida, M., Ishizaki, Y. and Iwahana, H.(1983)Biochem. Biophys. Res. Commun., 113, 562–568.
7. Silverman, D. H. S., Kreuger, J. M. and Karnovsky, M. L.(1986)J. Biol. Chem., 136, 2195–5501.
8. Pawelek, J. M. and Lerner, A. B.(1978)Nature, 276, 627–628.
9. Söderhäll, K. and Ajaxon, R.(1982)J. Invertebr. Pathol., 39, 105–109.
10. Nappi, A. J. and Vass, E.(1993)Pigment Cell Res., 6, 117–126.
11. Thörnqvist, P.-O., Johansson, M. W. and Söderhäll, K.(1994)Dev. Comp. Immunol., 18, 3–12.
12. Poinar, G. O., Jr. and Hess, R. T.(1977)in Comparative Pathobiology, Vol. 3(Bula, L. A. and Cheng, T. C., eds.) pp. 69–84, Plenum Press, N.Y..
13. Dales, R. P.(1983)J. Invertebr. Pathol., 42, 288–291.
14. Valembois, P., Lassègues, M. and Roch, P.(1992)Dev. Comp. Immunol., 16, 95–101.
15. Porchet-Hennerè, E. and Vernet, G.(1992)Cell Tissue Res., 269, 167–174.
16. Portchet-Hennerè, E. and M'Berri, M.(1987)J. Invertebr. Pathol., 50, 58–66.
17. Smith, V. J. and Söderhäll, K.(1991)Dev. Comp. Immunol., 15, 251–261.
18. Fischer, E.(1978)Acta Histochem., 63, 210–223.
19. Valembois, P. Seymour, J. and Roch, P.(1991)J. Invertebr. Pathol., 57, 177–183.
20. Paik, S. R., Cho, E. J. Kim, G. M. and Chang, C. S.(1994)Dev. Comp. Immunol. 18, S1222.
21. Bilej, M. Brys, L., Beschin, A., Lucas, R., Vercauteren, E., Hanusova, R. and De Baetselier, P.(1995) Immunol. Lett., 45, 123–128.
22. Fernandez, J., Andrews, L. and Mischee, S. M.(1994) Anal. Biochem., 218, 112–118.
23. Chomczynski, P. and Sacchi, N.(1987)Anal. Biochem., 162, 156–159.
24. Magez, S., Geuskens, M., Beschin, A., Del Favero, H., Verschueren, H., Lucas, R., Pays, E. and De Baetselier, P.(1997)J. Cell. Biol., 137, 715–727.
25. Lanham, S. N.(1968)Nature, 218, 1273–1274.

TABLE 1 aminoacid sequence of CCF-1 and TNF/TIP peptides

| Peptide | Amino acid sequence |
|---|---|
| CCF-1.1 | N-terminus: NH2-FTDWDQYHIVWQDEFDYFDGAKWQHEVTAT-COOH SEQ ID NO:8 |
| CCF-1.2 | (R,K)⁻ NH2-VYK-COOH SEQ ID NO:9 |
| CCF-1.4 | (R,K)⁻ NH2-NTGGEFLGIQK-COOH SEQ ID NO:10 |
| CCF-1.5 | (R,K)⁻ NH2-MGSTMHWGPGWDDNER-COOH SEQ ID NO:11 |
| CCF-1.8 | (R,K)⁻ NH2-YWLTSLPK-COOH SEQ ID NO:12 |
| CCF-1.10 (CCF-1/TIP) | (R,K)⁻ NH2-SGEIDIIETIGNR-COOH SEQ ID NO:13 |
| TNF/TIP | TPEGAEA SEQ ID NO:14 |

TABLE 2 trypanolytic activity of CF and CCF-1.

| CF tested[a] | Neutralizing antibody[d] (12C9) | % Trypanolysis | % Inhibition |
|---|---|---|---|
| 1. Total CF[b] | − | 97 | |
| | + | 10 | 90 |
| 2. CF flow through[b] (irrelevant IgG column) | − | 94 | |
| | + | 7 | 93 |
| 3. CF flow through[b] (12C9 column) | − | 30 | |
| | + | 2 | 94 |
| 4. Eluate (CCF-1)[c] (12C9 column) | − | 42 | |
| | + | 0 | 100 |

[a]CF and CF subfractions were purified by immunoaffinity on irrelevant IgG or 12C9 colunm and tested for trypanolytic activity in the trypanolysis assay (% trypanolysis was recorded after 2 hrs).
[b]Concentration used = 1 mg/ml.
[c]Concentration used = 4 μg/ml.
[d]12C9 antibody was added at a concentration of 10 μg/ml.

TABLE 3 inhibition of the trypanolytic activity (T. brucei) of CCF-1 and TNF-α by antibodies and carbohydrates

| Inhibitor[a] | CCF-1 mediated trypanolysis[b] | | TNF-α mediated trypanolysis[c] | |
|---|---|---|---|---|
| | % Lysis | % Inhibition | % Lysis | % Inhibition |
| None | 42 | — | 41 | — |
| N,N-diacetylchitobiose | 3 | 73 | 0 | 100 |
| Cellobiose | 49 | 0 | 41 | 0 |
| Polyclonal anti-TNF/TIP | 0 | 100 | 0 | 100 |
| Polyclonal IgG control | 46 | 0 | 43 | 0 |
| Monoclonal anti-TNF/TIP | 0 | 100 | 0 | 100 |
| Monoclonal IgG control | 49 | 0 | 41 | 0 |
| Monoclonal anti-CCF-1(12C9) | 0 | 100 | 1 | 98 |
| Monoclonal anti-TNF (1F31F3) | 44 | 0 | 41 | 0 |

[a]Inhibitors were added at a final concentration of 10 μg/ml.
[b]CCF-1 was added in the trypanolysis assay at a final concentration of 4 μg/ml.
[c]TNF-α was added in the trypanolysis assay at a final concentration of 1.000 U/ml.

TABLE 4 inhibition of the trypanolytic activity (*T. cruzi*) of CF by antibodies and carbohydrates

| Inhibitor[a] | CF-1 mediated trypanolysis[b] | |
|---|---|---|
| | % Lysis | % Inhibition |
| None | 62 | — |
| N,N'-diacetylchitobiose | 19 | 70 |
| Cellobiose | 67 | 0 |
| Monoclonal anti-CCF-1(12C9) | 30 | 52 |
| Monoclonal IgG control | 67 | 0 |

[a]Inhibitors were added at a final concentration of 10 µg/ml.
[b]CF was added in the trypanolysis assay at a final dilution of 1:4.000.

TABLE 5 inhibition of the cytolytic activity of CCF-1 (L929) by antibodies and carbohydrates

| Inhibitor[a] | CCF-1 mediated cytolysis[b] | |
|---|---|---|
| | % Lysis | % Inhibition |
| Experiment 1 | | |
| None | 72 | — |
| N,N'-diacetylchitobiose | 0 | 100 |
| Monoclonal anti-CCF-1(12C9) | 0 | 100 |
| Monoclonal anti-TNF/TIP | 0 | 100 |
| Experiment 2 | | |
| None | 66 | — |
| Monoclonal anti-CCF-1(12C9) | 14 | 79 |
| Monoclonal anti-CCF-1(7F1) | 0 | 100 |
| Monoclonal anti-CCF-1(6H1) | 0 | 100 |

[a]Inhibitors were added at a final concentration of 10 µg/ml
[b]CCF-1 was added in the L929 cytolysis assay at a final concentration of 4 µg/ml

TABLE 6 parasitaemia in mice treated with anti-CCF-1 mAbs (group of 10 mice)

| | Parasites × $10^6$/ml | |
|---|---|---|
| Day pi | Control mAb-treated | anti-CCF-1 treated |
| 3 | 104 | 135 |
| 4 | 129 | 194 |
| 5 | 64 | 84 |
| 6 | 2 | 2 |

TABLE 7 parasitaemia in untreated or CCF-1-treated mice (group of 4 mice)

| | Parasites × $10^6$/ml | |
|---|---|---|
| Day pi | untreated | rCCF-1 treated |
| 3 | 207 | 142 |
| 4 | 211 | 143 |
| 5 | 102 | 104 |
| 6 | 6 | 1.2 |

TABLE 8

Production of TNF-α by 2C11-12 activated with CCF-1

| µg/ml CCF-1 | pg/ml TNF-α |
|---|---|
| 40 | 5843 |
| 20 | 2483 |
| 10 | 1112 |
| 5 | 370 |
| 2.5 | 60 |
| 1.25 | 17 |
| 0.625 | Nd |

Nd: not detectable

TABLE 9

Production of TNF-α by C3H/J PECs activated with CCF-1

| | pg/ml TNF-α | |
|---|---|---|
| µg/ml CCF-1 | − IFN-γ | + IFN-γ |
| 40 | nd | 300 |
| 20 | nd | 130 |
| 10 | nd | 30 |
| 5 | nd | Nd |
| 2.5 | nd | Nd |
| 1.25 | nd | Nd |
| 0.625 | nd | Nd | nd: not detectable

What is claimed is:
1. An isolated peptide consisting of SEQ ID NO: 1.
2. An isolated or recombinant peptide consisting of SEQ ID NO: 3.

* * * * *

UNITED STATES PATENT AND TRADEMARK OFFICE
CERTIFICATE OF CORRECTION

PATENT NO. : 7,060,790 B1  
APPLICATION NO. : 09/596101  
DATED : June 13, 2006  
INVENTOR(S) : Patrick de Baetselier and Alain Beschin Page 1 of 1

It is certified that error appears in the above-identified patent and that said Letters Patent is hereby corrected as shown below:

On the title page:
In ITEM (56) REFERENCES CITED,
"Other Publications,"

| | |
|---|---|
| last entry in 2$^{nd}$ column, | change "PCT International Perliminary Examination Report," to --PCT International Preliminary Examination Report,-- |
| COLUMN 3, LINE 35, | change "(C)CCF-1" to --(C) CCF-1-- |
| COLUMN 12, LINE 14, | change "Poly A+RNA" to --Poly A$^+$RNA-- |
| COLUMN 12, LINE 17, | change "A+RNA." to --A$^+$RNA.-- |
| COLUMN 13, LINE 33, | change "3'end" to --3' end-- |
| COLUMN 16, LINE 47, | change "5×10$^5$2C11–12" to --5×10$^5$ 2C11–12-- |
| COLUMN 18, LINE 38, | change "IgG or 12C9 colunm" to --IgG or 12C9 column-- |

Signed and Sealed this

Thirtieth Day of September, 2008

JON W. DUDAS  
*Director of the United States Patent and Trademark Office*